(12) United States Patent
Shaw

(10) Patent No.: US 8,188,322 B2
(45) Date of Patent: *May 29, 2012

(54) METHANOL PRODUCTION PROCESS

(75) Inventor: John M. Shaw, Edmonton (CA)

(73) Assignee: Technology Convergence Inc., Kincardin, Ontario (CA)

( * ) Notice: Subject to any disclaimer, the term of this patent is extended or adjusted under 35 U.S.C. 154(b) by 132 days.

This patent is subject to a terminal disclaimer.

(21) Appl. No.: 12/731,768

(22) Filed: Mar. 25, 2010

(65) Prior Publication Data

US 2010/0240778 A1 Sep. 23, 2010

Related U.S. Application Data

(60) Division of application No. 12/141,135, filed on Jun. 18, 2008, now Pat. No. 7,714,176, which is a continuation of application No. 10/798,312, filed on Mar. 12, 2004, now abandoned, and a continuation-in-part of application No. 09/985,212, filed on Nov. 2, 2001, now Pat. No. 6,736,955.

(30) Foreign Application Priority Data

Oct. 1, 2001 (CA) .................................. 2357527

(51) Int. Cl.
C07C 29/48 (2006.01)

(52) U.S. Cl. ................. 568/910.5; 518/704; 518/708

(58) Field of Classification Search .............. 568/910.5; 518/704, 708
See application file for complete search history.

(56) References Cited

U.S. PATENT DOCUMENTS

| | | | |
|---|---|---|---|
| 3,763,205 A | 10/1973 | Green | |
| 3,920,717 A | 11/1975 | Marion | |
| 4,158,637 A | 6/1979 | Jones | |
| 4,203,915 A | 5/1980 | Supp et al. | |
| 4,218,389 A | 8/1980 | Jackson et al. | |
| 4,219,492 A | 8/1980 | Konoki et al. | |
| 4,235,800 A | 11/1980 | Pinto | |
| 4,277,416 A | 7/1981 | Grant | |
| 4,395,495 A | 7/1983 | Cummings | |
| 4,407,973 A | 10/1983 | Van Dijk et al. | |
| 4,464,483 A | 8/1984 | De Lathouder | |
| 4,476,249 A | 10/1984 | Avery | |
| 4,546,111 A | 10/1985 | Banquy | |
| 4,628,066 A | 12/1986 | Bonnell et al. | |
| 4,894,394 A | 1/1990 | Van Dijk et al. | |
| 4,910,228 A | 3/1990 | Lywood | |
| 4,927,856 A | 5/1990 | Elion | |
| 4,927,857 A | 5/1990 | McShea, III et al. | |
| 4,994,093 A | 2/1991 | Wetzel et al. | |
| 5,037,619 A | 8/1991 | Alagy et al. | |
| 5,063,250 A | 11/1991 | Murayama et al. | |
| 5,173,513 A | 12/1992 | Pinto | |
| 5,180,570 A | 1/1993 | Lee et al. | |
| 5,310,506 A | 5/1994 | Supp et al. | |
| 5,312,843 A | 5/1994 | Yamauchi et al. | |
| 5,342,702 A | 8/1994 | MacGregor | |
| 5,344,848 A | 9/1994 | Steinberg et al. | |
| 5,389,258 A | 2/1995 | Smis et al. | |
| 5,416,245 A | 5/1995 | MacGregor et al. | |
| 5,472,986 A | 12/1995 | Van Dijk | |
| 5,496,859 A | 3/1996 | Fong et al. | |
| 5,512,599 A | 4/1996 | Hiramatsu et al. | |
| RE35,377 E | 11/1996 | Steinberg et al. | |
| 5,690,482 A | 11/1997 | Shessel et al. | |
| 5,770,630 A | 6/1998 | Kowal et al. | |
| 5,980,782 A | 11/1999 | Hershkowitz et al. | |
| 5,998,489 A | 12/1999 | Kobayashi et al. | |
| 6,005,011 A | 12/1999 | Hanningsen | |
| 6,117,916 A | 9/2000 | Allam et al. | |
| 6,156,234 A | 12/2000 | Briscoe et al. | |
| 6,191,174 B1 | 2/2001 | Early et al. | |
| 6,214,314 B1 | 4/2001 | Abbott | |
| 6,218,439 B1 | 4/2001 | Kobayashi et al. | |
| 6,736,955 B2 | 5/2004 | Shaw | |

FOREIGN PATENT DOCUMENTS

| | | |
|---|---|---|
| CA | 1206949 A | 7/1986 |
| CA | 1233324 A | 3/1988 |
| CA | 1235580 A | 4/1988 |
| CA | 1241545 A | 9/1988 |
| CA | 1241666 A | 9/1988 |
| CA | 1242749 A | 10/1988 |
| CA | 1247651 A | 12/1988 |
| CA | 1258773 A | 8/1989 |
| CA | 1266279 A | 2/1990 |
| CA | 1267423 A | 4/1990 |
| CA | 2004218 A | 5/1990 |
| CA | 2034685 A | 7/1991 |

(Continued)

OTHER PUBLICATIONS

Kirk-Othmer: "Encyclopedia of Chemical Technology 4th edition" 1995, John Wiley & Sons, New York (US) XP002226757, p. 545, Fig. 4.

(Continued)

Primary Examiner — Elvis O Price
(74) Attorney, Agent, or Firm — Bereskin & Parr LLP/S.E.N.C.R.L., s.r.l.; Philip C. Mendes da Costa

(57) ABSTRACT

A process for the production of methanol comprises feeding a hydrocarbon feedstock to a partial oxidation reactor to produce a synthesis gas comprising hydrogen, carbon monoxide and carbon dioxide; subjecting the synthesis gas to methanol synthesis to produce a methanol product stream and a tail gas stream; separating the tail gas stream into at least two streams comprising a purge stream and a recycle stream, the recycle stream comprising a substantial portion of the tail gas stream; and, recycling the recycle stream to the partial oxidation reactor.

26 Claims, 4 Drawing Sheets

FOREIGN PATENT DOCUMENTS

| | | |
|---|---|---|
| CA | 2034731 A | 8/1991 |
| CA | 2060108 A | 1/1992 |
| CA | 1297677 A | 3/1992 |
| CA | 1297911 A | 3/1992 |
| CA | 1300175 A | 5/1992 |
| CA | 1330349 A | 6/1994 |
| CA | 2077880 A | 7/1994 |
| CA | 2112849 A | 7/1994 |
| CA | 2204389 A | 5/1996 |
| CA | 2204776 A | 5/1996 |
| CA | 2227128 A | 1/1998 |
| CA | 2210391 A | 4/1998 |
| CA | 2213025 A | 4/1998 |
| CA | 1340334 A | 1/1999 |
| CA | 2114205 A | 5/1999 |
| CA | 2061710 A | 8/1999 |
| JP | 07136462 A | 5/1995 |
| WO | 01/47846 A1 | 7/2001 |

OTHER PUBLICATIONS

Database CA Online Chemical Abstracts Service, Columbus, Ohio, US; Akahori, Hideo: "Fixation of carbon dioxide in waste gases and environmental-friendly electric power plants" retrieved from STN database accession No. 123:121897 XP002226758 & JP 07 136462, May 30, 1995, Tokyo Shibuara Electric Co.

METHANOL PRODUCTION PROCESS

CROSS REFERENCE TO RELATED APPLICATIONS

This application is a divisional application of U.S. patent application Ser. No. 12/141,135 filed on Jun. 18, 2008, which is allowed, which is a continuation application of U.S. patent application Ser. No. 10/798,312 filed on Mar. 12, 2004 which is a continuation-in-part of U.S. Pat. No. 6,736,955 filed on Nov. 2, 2001, which is allowed.

FIELD OF THE INVENTION

This invention relates to a method of methanol production having reduced emission of carbon dioxide.

BACKGROUND OF THE INVENTION

Methanol is a synthetic fuel which is produced from reactants which provide carbon, hydrogen and oxygen. There are various sources of each of these molecules. For example, the requisite carbon may be obtained from coal (see for example U.S. Pat. No. 4,476,249 Avery), natural gas (see for example U.S. Pat. No. 5,496,589 Fong et al.) and heavy hydrocarbons such as pitch and atmospheric and vacuum residues (see for example Canadian Patent Application No. 2,060,108 Naber). Similarly, the oxygen and hydrogen, which are combined with the carbon during the synthesis step to form methanol, may be obtained from various sources. These include electrolysis, as well as the water gas shift reaction. For example, Avery and U.S. Pat. No. 5,416,245 (McGregor et al.) disclosed the use of electrolysis to provide hydrogen and oxygen. In the case of Avery, the oxygen is added together with steam to a gasifier to produce carbon monoxide and hydrogen for synthesis (column 4, lines 46-50).

Methanol is advantageous as a substitute fuel for gasoline as well as diesel fuel since it is a cleaner burning fuel (i.e. the fuel is converted to carbon dioxide and water with fewer by-products being produced). The reduced emissions associated with methanol will not favor its production unless methanol can be produced in a cost effective manner. In the retail marketplace, methanol must be priced competitively with gasoline and diesel fuel to be a commercial alternative fuel.

The advantage of methanol being a low polluting fuel will be reduced, or potentially lost, if the process for producing methanol has substantial emissions of greenhouse gases. Typical commercial processes, which are in operation to date, produce about 600 to 1200 pounds of carbon dioxide per ton of methanol produced. Therefore, while the methanol produced by these processes may be relatively non-polluting compared to gasoline and diesel fuel when it is combusted, when considered with the manufacturing process, the production and use of methanol may in fact be a substantial source of greenhouse gases.

SUMMARY OF THE INVENTION

In accordance with the instant invention, a process for the production of methanol is provided which has a reduced emission of carbon dioxide as a by-product of the manufacturing process. In particular, in accordance with the instant invention, a process for the production of methanol may result in the emission of only 240 pounds of carbon dioxide per ton of methanol produced and, preferably, 120 pounds or less of carbon dioxide per ton of methanol produced. In one embodiment of the present invention, the process has a net consumption of $CO_2$. For example, the process may consume up to about 650 pounds of $CO_2$ per ton of methanol produced.

In accordance with one aspect of this invention, a partial oxidation reactor is utilized to produce the synthesis gas which is then subjected to methanol synthesis to produce methanol and a tail gas stream. The tail gas stream has unreacted synthesis gases (including carbon dioxide) therein. A purge stream is removed to prevent the build up of inert gases therein. The remainder of the stream, or essentially all of the remainder of the stream, is recycled to the partial oxidation reactor. In this way, carbon dioxide, as well as carbon monoxide and methane, may be recycled through the system essentially to extinction except for the purge stream. The amount of greenhouse gases emitted by the process effectively depends upon the relative size of the purge gas stream to the recycle stream. The larger of the recycle stream, the smaller the greenhouse gases that are emitted. The recycle stream may comprise up to 95 weight percent, and preferably from 50 to 95 weight percent of the tail gas stream, based on the weight of the tail gas stream.

In order to reduce the size of the purge stream, the introduction of inert gases into the system is reduced. To this end, the oxygen which is used in the partial oxidation reactor preferably comprises essentially pure oxygen. In prior art processes, air or oxygen enriched air is utilized. This results in the introduction of substantial quantities of nitrogen. Not only does this result in the need to increase the size of the process equipment to have the same through put of methanol, but it also requires a larger purge stream and the consequential emission of additional greenhouse gases.

Typically, methanol production processes utilize reformers to provide additional hydrogen to the synthesis gas to obtain the desired stoichiometric ratio of hydrogen to CO and $CO_2$. Reformers, such as steam reformers, require the introduction of substantial quantities of water into the process and may result in the production of additional carbon dioxide at the expense of carbon monoxide formation. However, in one embodiment of the instant invention, a reformer is used to consume hydrogen in the conversion of $CO_2$ to CO. This is the reverse of the current practice of operating a reformer. In accordance with another aspect of the instant invention, a hydrogen source other than reformers is utilized to adjust the hydrogen balance of the synthesis gas just ahead of the methanol reactor. Preferably, at least some of the hydrogen is obtained by electrolysis and more preferably essentially all of the hydrogen is obtained by electrolysis.

In a further preferred aspect of the instant invention, at least some of the electricity which is utilized in operating the electrolysis step is obtained as off-peak or valley power from a power grid. Typically, the power demand of a power grid varies throughout the day with the power demand from the grid being reduced at night when commercial and residential requirements are reduced. Not only may off-peak or valley power be obtainable at a reduced rate compared to peak demand time, but, in addition, the use of valley power may result in more efficient operation of power generating plants. For example, if it is necessary to reduce the electrical output of a power generation plant, then the efficiency of the plant may be reduced. Alternately, it may not be possible to reduce the power output of a generating plant thus resulting in the emission of greenhouse gases to produce power that is not required. Therefore, the use of valley power to run at least a portion of the electrolysis step may be highly beneficial. In fact, the oxygen and hydrogen produced by electrolysis such as at night may be stored in storage tanks so as to ensure a continuous supply of hydrogen and oxygen. Thus, if there is a power shortage during a peak demand period (e.g. during the day) then a continuous supply of hydrogen and oxygen may be provided. In this way, the feed of raw materials to produce a synthesis gas may be leveled to ensure a uniform continuous supply. In a further alternate embodiment, the electricity may be generated by running a fuel cell in reverse (i.e. a fuel cell may be operated to utilize an energy source such as electricity to produce hydrogen and oxygen).

Another advantage of the instant invention is that the amount of hydrogen produced by the process may in fact exceed the amount of hydrogen required to produce the desired stoichiometric balance of the synthesis gas which is fed to the methanol synthesizer. Accordingly, the process may in fact also produce hydrogen as a valuable commercial product.

Accordingly, in accordance with this invention there is provided a process for the production of methanol comprising:
 (a) feeding an amount of a hydrocarbon feedstock and an amount of an oxygen feedstock to a partial oxidation reactor to produce a partial oxidation reactor effluent comprising hydrogen, carbon monoxide and carbon dioxide;
 (b) electrolyzing water to produce hydrogen and oxygen and recovering at least a portion of the hydrogen to produce a hydrogen stream;
 (c) adding an amount of a hydrogen feedstock, at least a portion of which is obtained from the hydrogen stream, to the partial oxidation reactor effluent to produce a synthesis gas stream having a predetermined ratio of hydrogen to carbon monoxide;
 (d) subjecting the synthesis gas to methanol synthesis to produce a methanol product stream and a tail gas stream;
 (e) separating the tail gas stream into at least two streams comprising a purge stream and a recycle stream, the recycle stream comprising a substantial portion of the tail gas stream; and,
 (f) recycling the recycle stream to the partial oxidation reactor.

In one embodiment, the process further comprises reforming the partial oxidation reactor effluent prior to the hydrogen addition step to convert at least some of the carbon dioxide to carbon monoxide. Optionally, a carbon dioxide feed stream may be provided.

In another embodiment, the process further comprises the step of recovering at least a portion of the oxygen produced by electrolyzing water to produce at least a portion of the oxygen feedstock.

In another embodiment, the process further comprises the step of adjusting the amount of the oxygen feedstock to the amount of the hydrocarbon feedstock fed to the partial oxidation reactor such that the partial oxidation reactor effluent contains some unoxidized hydrocarbon feedstock. The partial oxidation reactor effluent may contain up to about 10 wt % of the unoxidized hydrocarbon feedstock based on the weight of the partial oxidation reactor effluent and, preferably, the partial oxidation reactor effluent contains less than about 4 wt % of the unoxidized hydrocarbon feedstock based on the weight of the partial oxidation reactor effluent.

In another embodiment, the process further comprises the step of adjusting the amount of the oxygen feedstock to the amount of the hydrocarbon feedstock fed to the partial oxidation reactor such that the synthesis gas, which is subjected to methanol synthesis, is essentially free of oxygen.

In another embodiment, the synthesis gas which is subjected to methanol synthesis has a ratio of hydrogen minus carbon dioxide mole fraction to carbon dioxide plus carbon monoxide mole fraction of from about 1:1 to about 3:1.

In another embodiment, the synthesis gas, which is subjected to methanol synthesis has a ratio of hydrogen minus carbon dioxide mole fraction to carbon dioxide plus carbon monoxide mole fraction is about 2:1.

In another embodiment, the tail gas stream contains nitrogen and the method further comprises separating at least a portion of the nitrogen from the waste gas stream such that the purge stream is nitrogen rich and the recycle stream is a nitrogen reduced waste gas stream.

In another embodiment, a membrane separator is used to separate the tail gas into the nitrogen reduced waste gas stream and the nitrogen rich purge stream.

In another embodiment, the process further comprises combusting the nitrogen rich purge stream to produce energy.

In another embodiment, the combustion of the purge stream produces heat that is used to preheat at least one of the feedstocks of the partial oxidation reactor.

In another embodiment, the combustion of the purge stream produces electricity that is preferably used to electrolyze water.

In another embodiment, the partial oxidation reactor produces waste heat and the waste heat is used to generate electricity.

In another embodiment, the electrolysis is conducted by running a fuel cell in reverse.

In another embodiment, essentially all of the hydrogen and the oxygen is obtained by electrolysis.

In another embodiment, at least a portion of electricity used to electrolyze the water is valley power.

In accordance with another aspect of the instant invention, there is provided a process for the production of methanol comprising:
 (a) feeding an amount of a hydrocarbon feedstock and an amount of an oxygen feedstock to a partial oxidation reactor to produce a partial oxidation reactor effluent comprising hydrogen, carbon monoxide and carbon dioxide;
 (b) adding an amount of a hydrogen feedstock to the partial oxidation reactor effluent to produce a synthesis gas stream having a predetermined ratio of hydrogen to carbon monoxide; and,
 (c) subjecting the synthesis gas to methanol synthesis to produce a methanol product stream and a tail gas stream wherein reformation is not used to provide hydrogen as a product.

In one embodiment, the process further comprises the step of recycling a portion of the tail gas stream to the partial oxidation reactor.

In another embodiment, the process further comprising the step of withdrawing a purge stream from the tail gas stream and recycling essentially the remainder of the tail gas stream to the partial oxidation reactor.

In accordance with another aspect of the instant invention, there is provided a process for the production of methanol comprising:
 (a) feeding a hydrocarbon feedstock to a partial oxidation reactor to produce a synthesis gas comprising hydrogen, carbon monoxide and carbon dioxide;
 (b) subjecting the synthesis gas to methanol synthesis to produce a methanol product stream and a tail gas stream;
 (c) separating the tail gas stream into at least two streams comprising a purge stream and a recycle stream, the recycle stream comprising a substantial portion of the tail gas stream; and,
 (d) recycling the recycle stream to the partial oxidation reactor.

In another embodiment, the tail gas stream contains nitrogen and step (c) comprises subjecting the tail gas stream to a separation process such that the recycle stream is nitrogen reduced and the purge stream is nitrogen rich.

In accordance with another aspect of the instant invention, a process for the production of methanol comprising:
(a) electrolyzing water to produce hydrogen and oxygen and recovering at least some of the hydrogen to produce a hydrogen stream and recovering at least some of the oxygen to produce an oxygen stream;
(b) feeding an amount of a hydrocarbon feedstock and an amount of an oxygen feedstock, at least a portion of which is obtained from the oxygen stream, to a partial oxidation reactor to produce an effluent gas stream comprising hydrogen, carbon monoxide and carbon dioxide;
(c) adding an amount of a hydrogen feedstock, at least a portion of which is obtained from the hydrogen stream, to the partial oxidation reactor effluent to produce a synthesis gas having a predetermined ratio of hydrogen to carbon monoxide;
(d) subjecting the synthesis gas to methanol synthesis to produce a methanol product stream and a tail gas stream:
(e) recycling a portion of the tail gas stream to the partial oxidation reactor; and,
(f) combusting the purge stream to obtain energy wherein reformation is not used to provide hydrogen as a product.

In one embodiment, the process further comprises combusting the nitrogen rich purge stream to produce energy.

In another embodiment, the combustion of the purge stream produces heat that is used to preheat at least one of the feedstocks of the partial oxidation reactor.

In another embodiment, the combustion of the purge stream produces electricity that is preferably used to electrolyze water.

In another embodiment, the partial oxidation reactor produces waste heat and the waste heat is used to generate electricity.

In another embodiment, the electrolysis is conducted by running a fuel cell in reverse.

In accordance with another embodiment of the instant invention, a process for the production of methanol comprises:
(a) feeding an amount of a hydrocarbon feedstock and an amount of an oxygen feedstock to a partial oxidation reactor to produce a partial oxidation reactor effluent comprising hydrogen, carbon monoxide and carbon dioxide;
(b) electrolyzing water to produce hydrogen and oxygen and recovering at least a portion of the hydrogen to produce a hydrogen stream;
(c) reacting carbon dioxide with hydrogen to produce carbon monoxide; and,
(d) subjecting a methanol synthesis gas obtained from the partial oxidation reactor effluent, at least a portion of the hydrogen stream and carbon monoxide produced by step (c) to methanol synthesis to produce a methanol product stream and a tail gas stream.

In one embodiment, the process as further comprises separating the tail gas stream into at least two streams comprising a purge stream and a recycle stream, the recycle stream comprising a substantial portion of the tail gas stream; and recycling the recycle stream to the partial oxidation reactor.

In another embodiment, the partial oxidation reactor effluent is fed to a reformer to produce a reformed synthesis gas and at least a portion of the hydrogen stream is combined with the reformed synthesis gas to produce the methanol synthesis gas.

In another embodiment, the process further comprises combining a carbon dioxide feedstock with the partial oxidation reactor effluent to produce a carbon dioxide rich synthesis gas stream and feeding the carbon dioxide rich synthesis gas stream to the reformer to produce a reformed synthesis gas.

In another embodiment, at least a portion of the hydrogen stream is combined with the reformed synthesis gas to produce the methanol synthesis gas.

In another embodiment, wherein at least a portion of the hydrogen stream is introduced to the reformer or a feedstream to the reformer.

In accordance with any aspect of this invention, the hydrocarbon feedstock may include carbon dioxide. In such a case, additional carbon dioxide may be provided by a carbon dioxide feed stream and at least a portion of the carbon dioxide stream is obtained from biogas. Alternately, the additional carbon dioxide may be provided by a carbon dioxide feed stream obtained from any standard source in the industry.

In accordance with any aspect of this invention the hydrocarbon feedstock is obtained from biogas and includes carbon dioxide. The carbon dioxide feed stream may be provided upstream from the partial oxidation reactor. Alternately, or in addition, the carbon dioxide feed stream is provided downstream from the partial oxidation reactor.

BRIEF DESCRIPTION OF THE DRAWINGS

These and other advantages of the instant invention may be more completely fully understood by means of the following description of the accompanying drawings of the preferred embodiments of the instant invention in which.

DETAILED DESCRIPTION OF THE INVENTION

Figure 1:
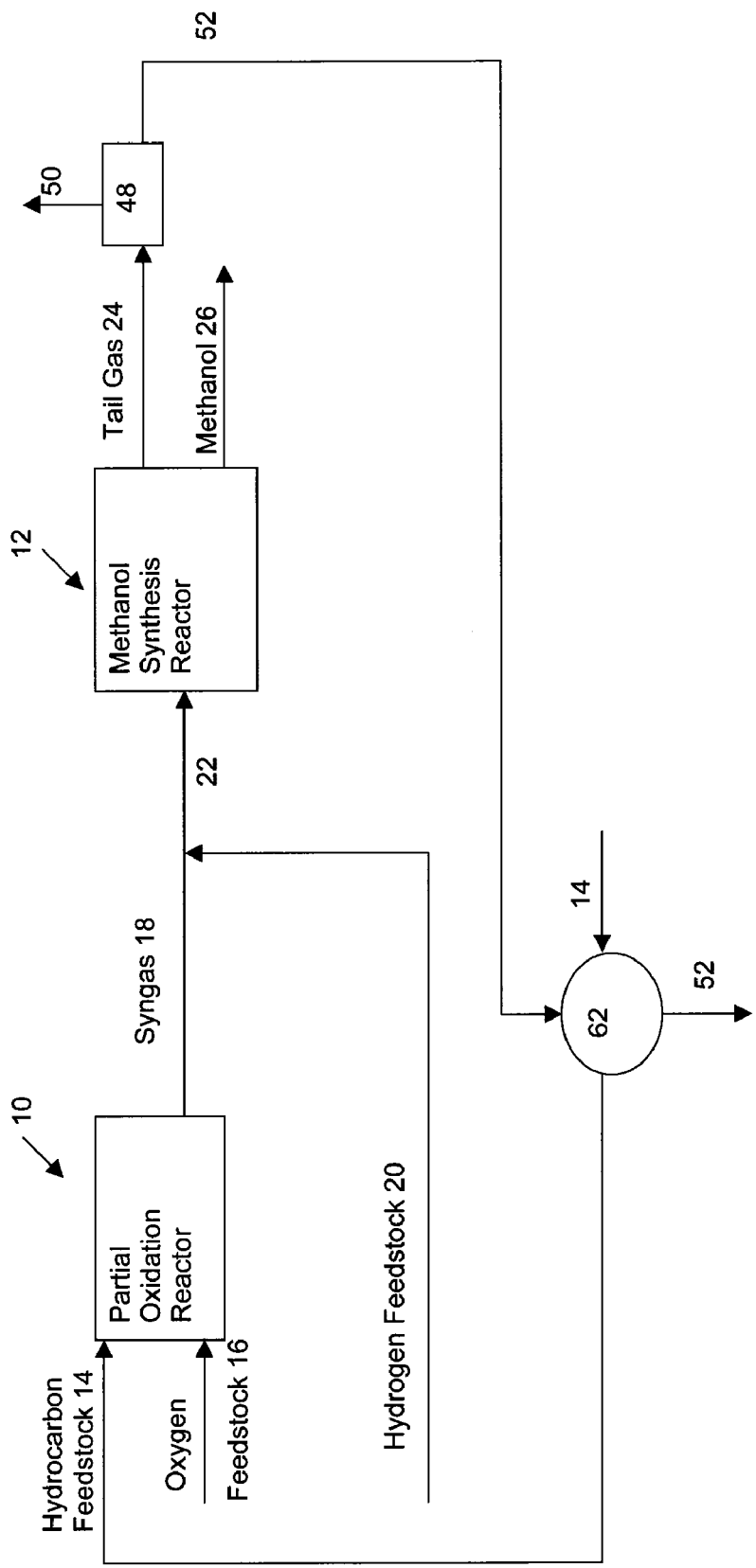
FIG. 1 is a schematic drawing of a preferred embodiment of the instant invention.

As shown in FIG. 1, according to a preferred embodiment of the instant invention, the process comprises partial oxidation reactor 10 and methanol synthesis reactor 12. Hydrocarbon feedstock 14 and oxygen feedstock 16 are fed to partial oxidation reactor 10 to produce synthesis gas 18. Hydrogen feedstock 20 is combined with synthesis gas 18 to produce synthesis gas 22 wherein the stoichiometric balance has been adjusted. The adjusted synthesis gas 22 is fed to methanol synthesis reactor 12 to produce tail gas 24 and methanol 26.

In steam reformation processes, steam is added to a reformer. Further, the hydrocarbon feedstock fed to the stream reformer may be humidified (which provides a further source of water). Overall, the process gas streams contain substantial quantities of water and the methanol produced typically is treated such as by distillation to reduce the water content of the methanol. In accordance with one embodiment of the instant process a hydrogen gas stream which is relatively pure (e.g. more than about 97 weight percent hydrogen and more preferably more than about 99 weight percent hydrogen) is preferably utilized to adjust the chemical balance of the synthesis gas. In accordance with this embodiment, water need not be added to the process and is preferably not added to the process (except in so far as some quantities may be contained with the hydrocarbon feedstock such as may be contained for example in natural gas). Accordingly, the amount of water traveling through the process and accordingly exiting methanol synthesis reactor 12 is substantially reduced compared to steam reformation processes. Accordingly, methanol 26 may have a relatively low level of water.

Methanol which contains as much as 10 weight percent water may be burned in convention combustion devices such as an internal combustion engine. In accordance with this embodiment of the instant invention, by avoiding the use of reformation in the process, methanol 26 (which is the product produced directly from methanol synthesis reactor 12 without distillation) may contain less than this amount of water and accordingly, may be a commercial product without further processing. More preferably, methanol stream 26 contains less than 6 weight percent water and, more preferably, less than about 2 weight percent water.

Hydrocarbon feedstock 14 may be any gaseous or liquid hydrocarbon, is preferably a gaseous hydrocarbon and, more preferably comprises a substantial quantity of methane (e.g. more than 90 weight percent). In one particular embodiment, hydrocarbon feedstock 14 preferably comprises and, more preferably, consists essentially of natural gas or methane. In an alternate preferred embodiment, some or all of the hydrocarbon feedstock may be obtained from biomass. Biomass may comprise one or more of manure, silage, agricultural waste, peat and organic household waste. Many sources of biomass are known to those skilled in the waste disposal art. The anaerobic decomposition of biomass produces biogas which comprises one or more of methane, carbon dioxide, hydrogen, hydrogen sulfide, nitrogen and other components. The actual composition of the biogas will vary depending upon the biomass which is used as a feedstock and if any oxygen is present (in which case some aerobic decomposition will occur). If biogas is used as a feedstock, then some pollutants such as hydrogen sulfide are preferably removed by any separation technique known in the art prior to the biogas being used as a feedstock for the methanol production process described herein. Alternately, or in addition, the biogas may be treated to obtain a methane stream. The biogas, or a methane stream obtained from the biogas, may be used as a source of some or all of the hydrocarbon required for the methanol production process and may be fed to the process in any manner disclosed herein. For example such a methane stream and/or the biogas may form part or all of hydrocarbon feedstock 14.

Figure 2:
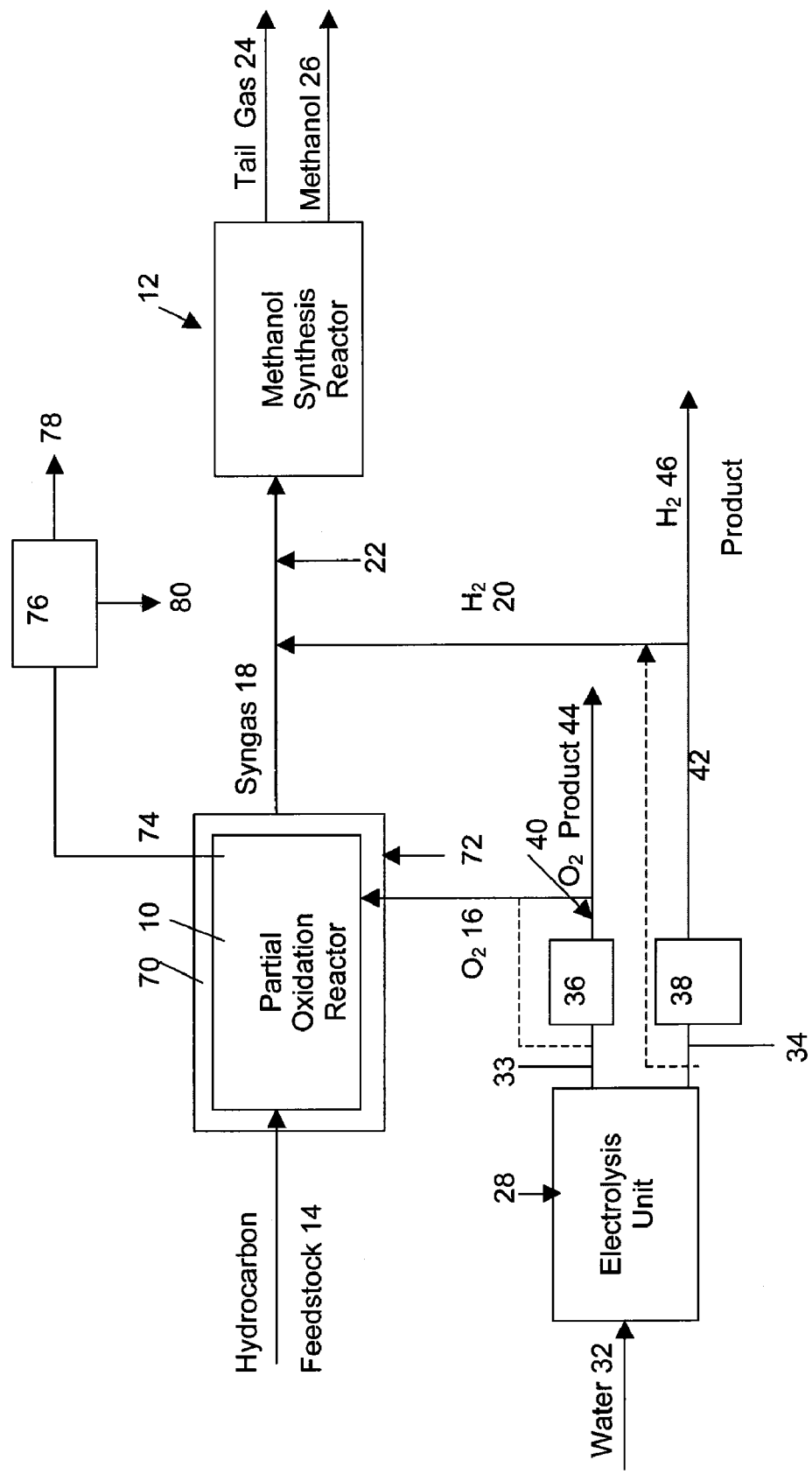
FIG. 2 is a schematic drawing of an alternate preferred embodiment in accordance with the instant invention.

As shown in FIG. 2, oxygen feedstock 16 may be obtained by electrolysis. In particular, water 32 is feed to electrolysis unit 28 to produce oxygen stream 16 and hydrogen stream 34. Some or all of oxygen stream 16 may be fed directly to partial oxidation reactor 10 as oxygen stream 16' (as shown by the broken feed line shown in FIG. 2). Similarly, some or all of hydrogen stream 34 may be fed directly to synthesis gas 18 as hydrogen stream 20 (as shown by the broken feed line shown in FIG. 2). Preferably, storage tanks are utilized to produce a generally continuous flow of hydrogen and oxygen to streams 16' and 20. To this end, one or more oxygen storage tanks 36 and one or more hydrogen storage tanks 38 may be provided.

In operation, electricity for electrolysis unit 28 may be obtained from a power grid. During peak periods, when the cost of electricity is greater or, in some cases, when the requisite amount of electricity may not be available, the production of hydrogen and oxygen by electrolysis unit 28 may be reduced. In such cases, the amount of hydrogen and oxygen delivered to storage tanks 36 and 38 is reduced. However, depending upon the capacity of storage tanks 36 and 38, the process may be supplied with hydrogen and oxygen via streams 42 and 40 at about the same rate regardless of the flow rate of hydrogen and oxygen into tanks 36 and 38 via streams 33 and 34. In this way, tanks 36 and 38 may be utilized to produce a continuous flow of hydrogen and oxygen to the process.

In another embodiment of the instant invention, electrolysis unit 28 may produce excess hydrogen and oxygen then are required for the operation of partial oxidation and methanol synthesis reactors 10 and 12. In such cases, the excess amounts may be withdrawn as product oxygen stream 44 and/or product hydrogen stream 46. Alternately, or in addition, some or all of the hydrogen may be obtained from biogas. For example, a biogas may be treated to obtain a hydrogen stream which may be used, e.g., as all or part of hydrogen feedstock stream 20. Alternately, or in addition, if a biogas is used to provide some or all of the hydrocarbon requirement, then hydrogen may be provided with the biogas which supplies the hydrocarbon requirement. For example, if biogas is used to provide part or all of hydrocarbon feedstock stream 14, then the biogas may be treated to remove pollutants leaving a stream containing methane and hydrogen. Alternately, the biogas may be treated to produce a stream containing methane and hydrogen.

In one embodiment, synthesis gas 22 has a ratio of hydrogen minus carbon dioxide mole fraction to carbon dioxide plus carbon monoxide mole fraction of from about 1.1 to about 3.1 and, preferably, the ratio is about 2.1. To achieve these ratios, particularly if hydrocarbon feedstock 14 substantially comprises or consists essentially of methane, a greater proportion of the oxygen produced by electrolysis unit 28 will be required then the hydrogen produced by electrolysis unit 28. Accordingly, then in one embodiment of operation, electrolysis unit 28 may be operated to produce essentially the requisite amount of oxygen to produce this ratio resulting in essentially no product oxygen stream 44. However, as less hydrogen will be required to produce the desired ratio, only a portion of the hydrogen produced by electrolysis unit 28 need be combined with synthesis gas 18 via stream 20. Accordingly, the overall process will be a net producer of not only methanol but also hydrogen as well via stream 46.

In accordance with another aspect of the instant invention, the process is preferably operated such that synthesis gas 22 essentially contains no oxygen (e.g. less than about 0.5 weight percent). If the oxygen content of the synthesis gas is too high, then oxygen will react with methanol in methanol synthesis reactor 12 to form carbon dioxide and water. To reduce the amount of oxygen in the synthesis gas, the amount of hydrocarbon feedstock 14 fed to partial oxidation reactor 10 is preferably adjusted, based upon the flow rate of oxygen stream 16 to partial oxidation reactor 10 such that the effluent from partial oxidation reactor 10 contains at least some unoxidized hydrocarbon feedstock. Preferably, the effluent contains from less than about 10 weight percent of the unoxidized hydrocarbon feedstock and, more preferably, less than about 4 weight percent of the unoxidized hydrocarbon feedstock, based on the weight of the effluent stream. At these levels, essentially all of the oxygen will be utilized in partial oxidation reactor 10. It will be appreciated by those skilled in the art that the actual amount of unoxidized hydrocarbon which is required will vary in part depending upon the efficiency of partial oxidation reactor 10.

Figure 3:
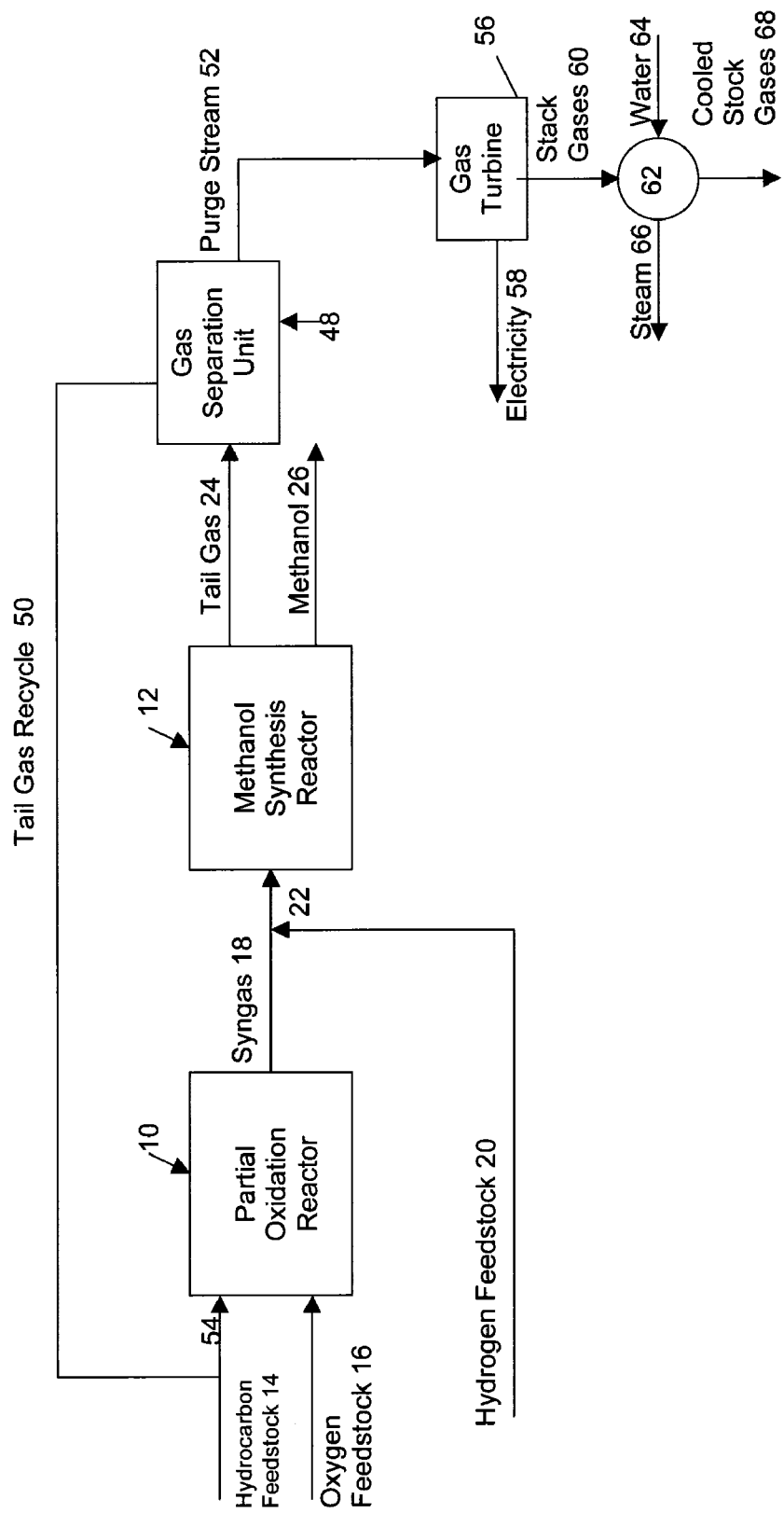
FIG. 3 is a schematic drawing of a further alternate preferred embodiment in accordance with the instant invention; and, FIG. 4 is a schematic drawing of a further alternate preferred embodiment in accordance with the instant invention.

Referring to FIG. 3, in a further embodiment of the instant invention, tail gas stream 24 is subjected to gas separation unit 48 to produce tail gas recycle stream 50 and purge stream 52. Preferably, gas separation unit 48 utilizes cryogenic separation or a membrane separator and, more preferably, a membrane separator. Purge stream 52 is utilized to remove inert material such as nitrogen, argon and the like. The inert material that is to be removed will vary depending upon the contaminants in the feedstocks. For example, if hydrocarbon feedstock stream 14 is natural gas, purge stream 52 is utilized to remove, for example, nitrogen that is present with the natural gas. The substantial portion of the tail gas is recycled as recycle stream 50. In particular, recycle stream 50 may comprise up to about 95 weight percent and, more preferably from about 50 to about 95 weight percent of tail gas stream 24. Accordingly, a substantial portion of an unreacted synthesis gas is recycled into the system. As shown in FIG. 3, recycle stream 50 is preferably combined with hydrocarbon feedstock stream 14 to produce blended hydrocarbon stream 54 which is then fed to partial oxidation reactor 10. Alternately, recycle stream 50 may be fed directly to partial oxidation reactor 10. In either case, the unreacted synthesis gases, which include carbon dioxide, is recycled through the partial oxidation reactor wherein some of the carbon dioxide may be converted to carbon monoxide which is then combined with hydrogen in the methanol synthesis reactor 12 to produce methanol. The conversion of the carbon dioxide to carbon monoxide may occur in an optional reformer 46. However, at the high temperatures of the gasses, this reaction may also occur to an extent in the fluid conduits in which the gasses are at a sufficiently high temperature (e.g. synthesis gas effluent 18 from partial oxidation reactor 10) and in heat exchangers.

Purge stream 52 may be fed to a combustion unit 56, such as a gas turbine, to produce power 58 and stack gases 60. Power 58 may be in the form of mechanical power or electricity if combustion unit 56 is drivingly connected to a generator.

Stack gases will be at an elevated temperature. Accordingly, excess heat from stack gases 60 may be recovered by means of heat exchanger 62. For example, water 64 may be fed to heat exchanger 62 to indirectly heat the water to produce steam 66 and cooled stack gases 68. In an alternate embodiment, shown in FIG. 1, purge gas 52 may be utilized to preheat a feedstock, e.g. hydrocarbon feedstock 14. In such a case, purge stream 52 may be fed directly to indirect exchanger 62 or it may first be fed to combustion unit 56 to further increase the temperature of the purge stream prior to the heat exchange step.

In a further alternate embodiment shown in FIG. 2, the excess heat generated by partial oxidation reactor 10 may be recovered to produce steam and, more preferably electricity. For example, referring to FIG. 2, partial oxidation reactor 10 may be provided with a jacket (e.g. a cooling jacket fed with water 72). The water is heated and thus moderates the temperature of partial oxidation reactor 10. The water may be heated by its passage through jacket 70 to such an extent that it produces stream 74 which may be steam. Alternately, stream 74 may be superheated water which, upon passage though turbine 76 produces electricity 78 and water or wet steam 80.

Figure 4:
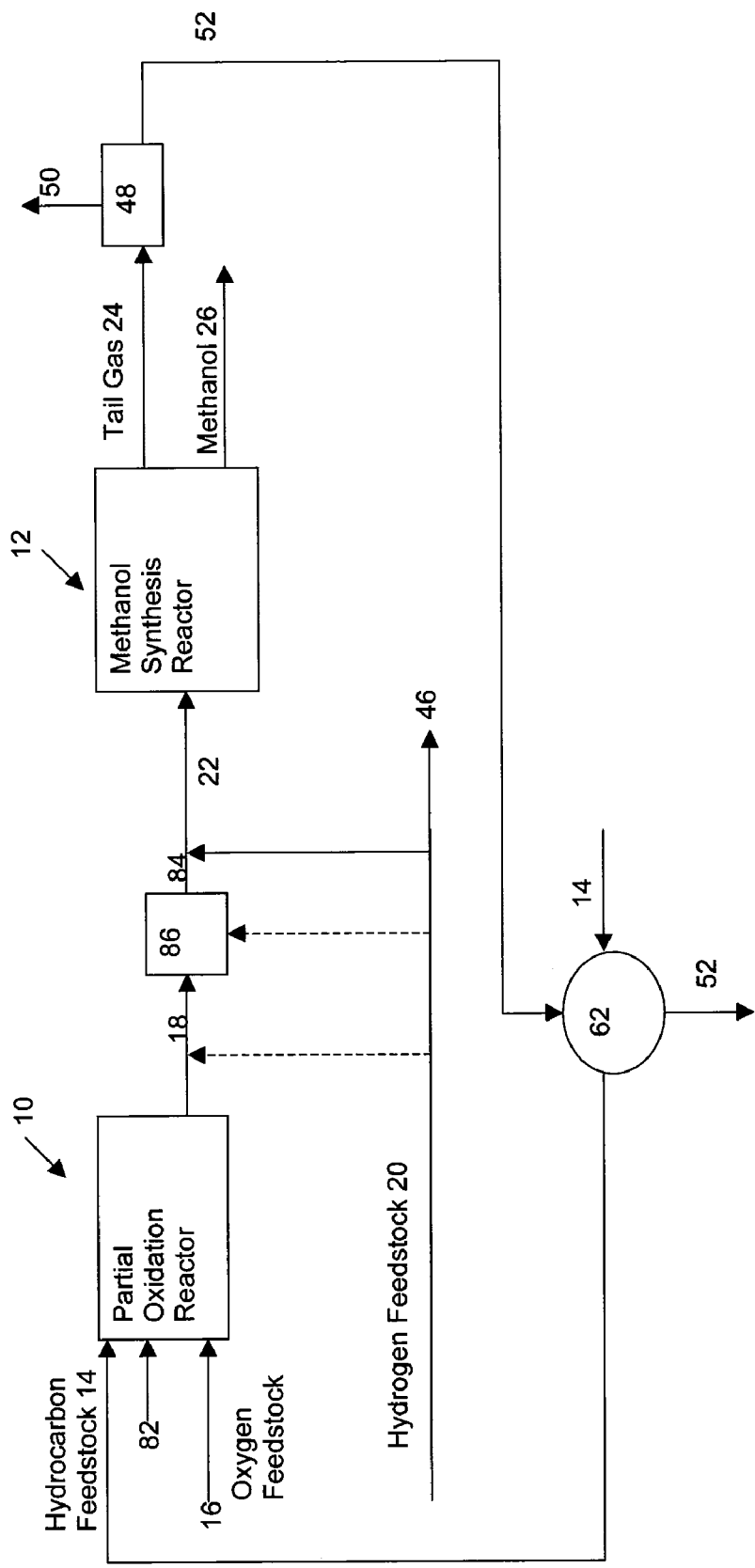

In accordance with another embodiment of the instant invention, carbon dioxide in synthesis gas 18 and/or carbon dioxide from a feedstock 82 is converted to carbon monoxide to provide additional feed gas for conversion to methanol (see FIG. 4). Pursuant to this embodiment, reformer 86 is provided downstream from partial oxidation reactor 10. Synthesis gas 18 is fed to reformer 86. Conventionally, a reformer is operated to provide hydrogen as a product. In accordance with this embodiment, reformer 86 is operated to convert carbon dioxide to carbon monoxide by the overall reaction:

$$CO_2 + H_2 \rightarrow CO + H_2O$$

Accordingly, hydrogen from one of the feedstocks is consumed by the process. As discussed previously, the instant process may be conducted to produce product hydrogen stream 46. According to this embodiment, at least a portion of the product hydrogen stream could effectively be used by reformer 86. In this way, the amount of product hydrogen stream 46 may be reduced or eliminated depending on the amount of hydrogen required for reformer 86. By operating a reformer effectively in reverse, the product of the reformer (reformed synthesis gas stream 84) will contain water. Typically, reformer 86 will be operated at a pressure less than methanol synthesis reactor 12 and at a higher temperature. As the temperature of reformed synthesis gas stream 84 is reduced and the pressure is increased so that reformed synthesis gas stream 84 is suitable for feeding to methanol synthesis reactor 12, water may be removed from reformed synthesis gas stream 84. In this way, water production is shifted away from methanol synthesis reactor 12 and the purity of the product methanol stream 26 is increased.

The carbon dioxide for reformer 86 may be supplied from synthesis stream 18. Alternately, or in addition, a carbon dioxide feedstock stream 82 may be provided. Carbon dioxide feedstock stream 82 may be obtained from various sources and is preferably relatively pure since any contaminants will have to be purged from the system or will contaminate the methanol produced by the process. Carbon dioxide feedstock stream 82 may be obtained as excess carbon dioxide from a bottling plant or as exhaust gas produced by combustion. In the later case, the exhaust gas is preferably subjected to cleaning steps to remove undesirable contaminants. The carbon dioxide is preferably obtained as a by product of another process so that the instant process becomes effectively a temporary carbon sink to convert carbon dioxide, which would otherwise be released to the atmosphere, to a stored carbon source. For example, some or all of the carbon dioxide may be obtained from biogas. In one embodiment, a biogas may be treated to obtain a carbon dioxide stream which may be used, e.g., as all or part of carbon dioxide stream 82. Alternately, or in addition, if biogas is used to provide part or all of hydrocarbon feedstock stream 14, then the biogas may be treated to remove pollutants leaving a stream containing methane and carbon dioxide. Alternately, the biogas may be treated to produce a stream containing methane and carbon dioxide.

Reformed synthesis gas stream 84 may be treated as discussed previously. Alternately, hydrogen may be added to the process upstream of reformer 86 (as shown by the dashed line in FIG. 4) or directly to reformer 84 (as shown by the dashed line in FIG. 4).

It will be appreciated by those skilled in the art that each of the embodiments of the instant invention may be utilized individually or combined to produce an improved process for the production of methanol.

The invention claimed is:
1. A process for the production of methanol comprising:
 (a) feeding a hydrocarbon feedstock to a partial oxidation reactor to produce a synthesis gas comprising hydrogen, carbon monoxide and carbon dioxide;
 (b) subjecting the synthesis gas to methanol synthesis to produce a methanol product stream and a tail gas stream;

(c) separating the tail gas stream into at least two streams comprising a purge stream and a recycle stream, the recycle stream comprising a substantial portion of the tail gas stream; and, (d) recycling the recycle stream to the partial oxidation reactor.

2. The process as claimed in claim 1 wherein the tail gas stream contains nitrogen and step (c) comprises subjecting the tail gas stream to a separation process such that the recycle stream is nitrogen reduced and the purge stream is nitrogen rich.

3. The process as claimed in claim 1 wherein at least a portion of at least one of the hydrocarbon feedstock, the hydrogen in the synthesis gas and the carbon dioxide in the synthesis gas is obtained from biogas.

4. The process as claimed in claim 1 wherein the hydrocarbon feedstock includes carbon dioxide.

5. The process as claimed in claim 4 wherein additional carbon dioxide is provided by a carbon dioxide feed stream and at least a portion of the carbon dioxide stream is obtained from biogas.

6. The process as claimed in claim 4 wherein additional carbon dioxide is provided by a carbon dioxide feed stream.

7. The process as claimed in claim 1 wherein the hydrocarbon feedstock is obtained from biogas and includes carbon dioxide.

8. The process as claimed in claim 7 wherein the carbon dioxide feed stream is provided upstream from the partial oxidation reactor.

9. The process as claimed in claim 7 wherein the carbon dioxide feed stream is provided downstream from the partial oxidation reactor.

10. The process as claimed in claim 1 wherein the biogas is obtained from anaerobic decomposition of biomatter.

11. A process for the production of methanol comprising:
(a) feeding an amount of a hydrocarbon feedstock and an amount of an oxygen feedstock to a partial oxidation reactor to produce a partial oxidation reactor effluent comprising hydrogen, carbon monoxide and carbon dioxide;
(b) electrolyzing water to produce hydrogen and oxygen and recovering at least a portion of the hydrogen to produce a hydrogen stream;
(c) reacting carbon dioxide with hydrogen to produce carbon monoxide; and,
(d) subjecting a methanol synthesis gas obtained from the partial oxidation reactor effluent, at least a portion of the hydrogen stream and carbon monoxide produced by step (c) to methanol synthesis to produce a methanol product stream and a tail gas stream.

12. The process as claimed in claim 11 further comprising separating the tail gas stream into at least two streams comprising a purge stream and a recycle stream, the recycle stream comprising a substantial portion of the tail gas stream; and recycling the recycle stream to the partial oxidation reactor.

13. The process as claimed in claim 11 wherein the partial oxidation reactor effluent is fed to a reformer to produce a reformed synthesis gas and at least a portion of the hydrogen stream is combined with the reformed synthesis gas to produce the methanol synthesis gas.

14. The process as claimed in claim 11 further comprising combining a carbon dioxide feedstock with the partial oxidation reactor effluent to produce a carbon dioxide rich synthesis gas stream and feeding the carbon dioxide rich synthesis gas stream to the reformer to produce a reformed synthesis gas.

15. The process as claimed in claim 14 wherein at least a portion of the hydrogen stream is combined with the reformed synthesis gas to produce the methanol synthesis gas.

16. The process as claimed in claim 14 wherein at least a portion of the hydrogen stream is introduced to the reformer or a feedstream to the reformer.

17. The process as claimed in claim 11 wherein at least a portion of electricity used to electrolyze the water is valley power.

18. The process as claimed in claim 11 wherein at least a portion of at least one of the hydrocarbon feedstock and the hydrogen feedstock is obtained from biogas.

19. The process as claimed in claim 11 wherein additional carbon dioxide is provided by a carbon dioxide stream and at least a portion of the carbon dioxide stream is obtained from biogas.

20. The process as claimed in claim 11 wherein the hydrocarbon feedstock includes carbon dioxide.

21. The process as claimed in claim 20 wherein additional carbon dioxide is provided by a carbon dioxide feed stream and at least a portion of the carbon dioxide stream is obtained from biogas.

22. The process as claimed in claim 20 wherein additional carbon dioxide is provided by a carbon dioxide feed stream.

23. The process as claimed in claim 11 wherein the hydrocarbon feedstock is obtained from biogas and includes carbon dioxide.

24. The process as claimed in claim 23 wherein the carbon dioxide feed stream is provided upstream from the partial oxidation reactor.

25. The process as claimed in claim 23 wherein the carbon dioxide feed stream is provided downstream from the partial oxidation reactor.

26. The process as claimed in claim 11 wherein the biogas is obtained from anaerobic decomposition of biomatter.

* * * * *